US009566417B1

(12) United States Patent
Propp

(10) Patent No.: US 9,566,417 B1
(45) Date of Patent: Feb. 14, 2017

(54) INTEGRATED ANTIMICROBIAL DRESSING

(75) Inventor: Donald J. Propp, Dewitt, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 790 days.

(21) Appl. No.: 12/956,473

(22) Filed: Nov. 30, 2010

Related U.S. Application Data

(63) Continuation-in-part of application No. 12/821,420, filed on Jun. 23, 2010, now Pat. No. 8,486,004.

(60) Provisional application No. 61/222,511, filed on Jul. 2, 2009.

(51) Int. Cl.
*A61M 25/02* (2006.01)
*A61L 15/58* (2006.01)

(52) U.S. Cl.
CPC ............... *A61M 25/02* (2013.01); *A61L 15/58* (2013.01); *A61M 2025/024* (2013.01); *A61M 2025/0266* (2013.01)

(58) Field of Classification Search
CPC ............ A61M 25/02; A61M 2025/024; A61M 2025/0266; A61F 13/0203; A61L 15/58
USPC .......... 602/54; 604/174, 177, 180, 306, 332
See application file for complete search history.

(56) References Cited

U.S. PATENT DOCUMENTS

| | | | |
|---|---|---|---|
| 3,918,446 A | 11/1975 | Buttaravoli | |
| 4,615,334 A * | 10/1986 | Jaeger | 600/195 |
| 4,633,863 A * | 1/1987 | Filips et al. | 128/846 |
| 4,641,643 A * | 2/1987 | Greer | 128/888 |
| 4,793,486 A * | 12/1988 | Konopka et al. | 206/438 |
| 4,915,694 A * | 4/1990 | Yamamoto et al. | 604/180 |
| 5,295,950 A * | 3/1994 | Godley | 602/53 |
| 5,686,096 A * | 11/1997 | Khan et al. | 424/443 |
| 5,885,254 A * | 3/1999 | Matyas | 604/180 |
| 6,124,521 A * | 9/2000 | Roberts | 602/54 |
| 6,998,511 B2 | 2/2006 | Worthley | |
| 7,025,749 B2 * | 4/2006 | Propp | 604/180 |
| 7,294,752 B1 * | 11/2007 | Propp | 602/58 |
| 7,744,572 B2 | 6/2010 | Bierman | |
| 8,212,101 B2 * | 7/2012 | Propp | 602/58 |

(Continued)

OTHER PUBLICATIONS

Non-Final Office Action dated Apr. 8, 2015 for U.S. Appl. No. 13/932,170.

(Continued)

*Primary Examiner* — Bhisma Mehta
*Assistant Examiner* — Matthew A Engel
(74) *Attorney, Agent, or Firm* — Kristin L. Murphy; Brooks Kushman P.C.

(57) ABSTRACT

A dressing includes a transparent film layer having a top side, an opposite bottom side, and an insertion site viewing portion. The bottom side has an adhesive portion and an adhesive-free portion. The adhesive-free portion is disposed within the viewing portion. An antimicrobial member having a top side and an opposite bottom side is disposed in the viewing portion. A portion of the antimicrobial member is adhered to the film layer adhesive portion, and a portion of the antimicrobial member is disposed in the adhesive-free portion. The antimicrobial member includes an outer edge and an opening disposed within the outer edge. The opening is disposed in the adhesive-free portion. A catheter extending from an insertion site is receivable through the opening in the antimicrobial member. The antimicrobial member surrounds the insertion site when the dressing is applied to a patient.

24 Claims, 8 Drawing Sheets

(56) References Cited

U.S. PATENT DOCUMENTS

| | | | |
|---|---|---|---|
| 2005/0027258 A1* | 2/2005 | Bierman et al. | 604/174 |
| 2005/0249791 A1* | 11/2005 | Hobbs et al. | 424/443 |
| 2007/0055205 A1* | 3/2007 | Wright et al. | 604/174 |
| 2009/0036835 A1 | 2/2009 | Bierman | |
| 2009/0149814 A1 | 6/2009 | Bailey et al. | |
| 2009/0192470 A1* | 7/2009 | Propp | 604/180 |
| 2011/0282291 A1 | 11/2011 | Ciccone | |
| 2012/0109070 A1* | 5/2012 | Elsamahy et al. | 604/179 |

OTHER PUBLICATIONS

Response to Non-Final Office Action dated Apr. 8, 2015 for U.S. Appl. No. 13/932,170.

* cited by examiner

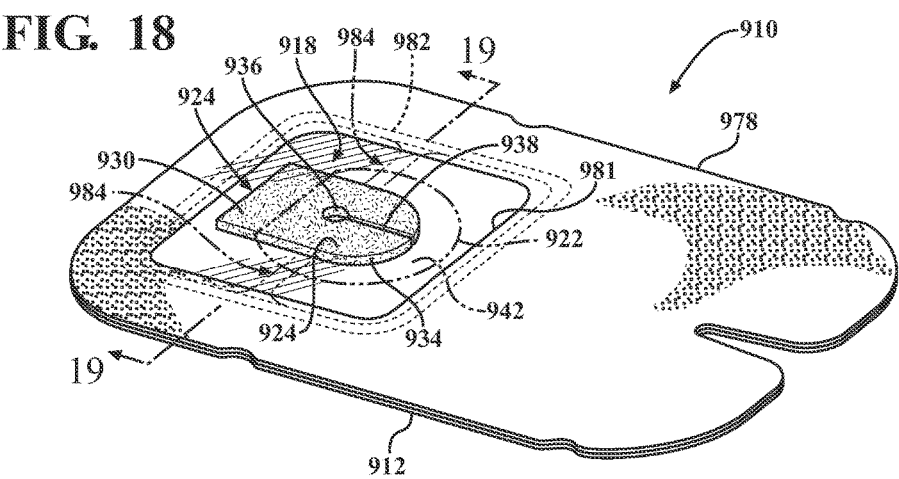
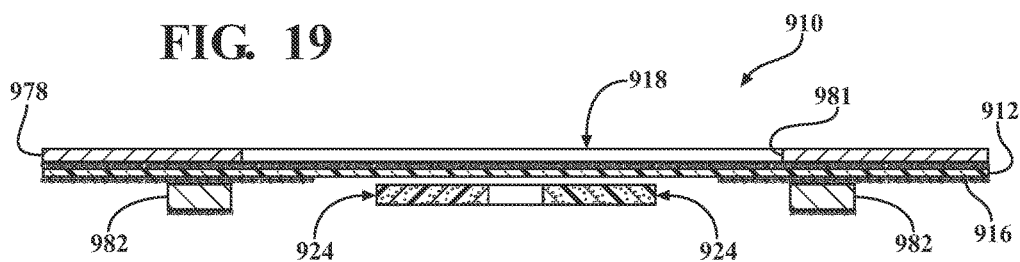
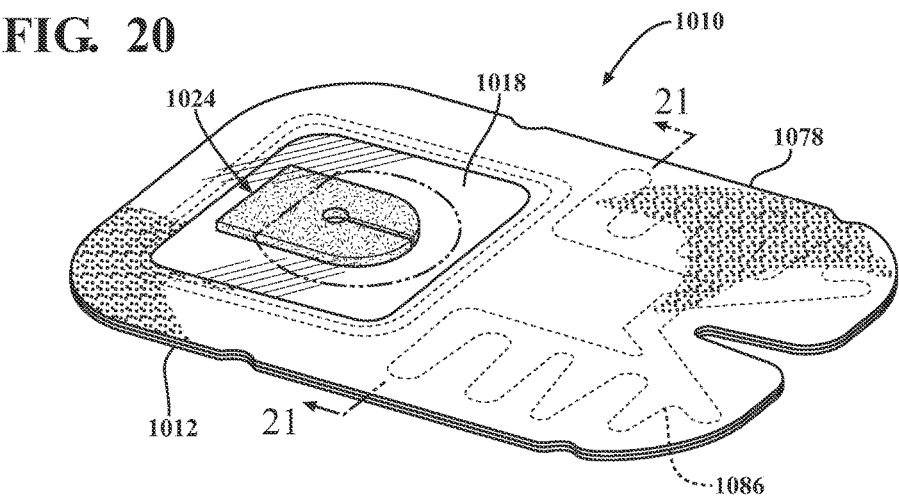

INTEGRATED ANTIMICROBIAL DRESSING

CROSS REFERENCE TO RELATED APPLICATIONS

This application is a continuation-in-part of U.S. patent application Ser. No. 12/821,420 filed Jun. 23, 2010, which claims the priority of U.S. Provisional Application No. 61/222,511 filed Jul. 2, 2009.

TECHNICAL FIELD

This invention relates to medical dressings, and more particularly to self-adherent catheter care dressings for the viewing and protection of PIA, PIV, PICC, CVC, IJ, subclavian, epidural, femoral, implant port catheters, and similar catheters about a catheter insertion site.

BACKGROUND OF THE INVENTION

It is known in the art relating to medical dressings for the protection and securement of catheters to apply a dressing to a patient's skin to cover a catheter insertion site at which the catheter punctures a patient's skin. It is also a conventional practice for medical clinicians (i.e., doctors, nurses, and other medical personnel) to separately apply an antimicrobial material (patch, liquid, ointment, etc.) at, around, or over the insertion site to protect the insertion site against the risk of viral or bacterial colonization and infection.

However, conventional antimicrobial materials are cumbersome to use with catheter insertion site dressings because the antimicrobial material is separate from the dressing and must be applied prior to the positioning of the dressing over the insertion site. Further, some antimicrobial materials do not adequately protect all the surface area of a patient's skin around the catheter, due to the catheter hub, or catheter lumen itself, holding the antimicrobial dressing/material up and away from the patient's skin, resulting in no contact "tenting" areas. Such an incomplete, or insufficient reach, of the antimicrobial device's zone of inhibition decreases the effectiveness of the antimicrobial material. Hence, conventional antimicrobial materials do not always fully, consistently, reliably, and sufficiently protect catheter insertion sites against infection. Further, additional labor and material costs of two dressings/devices are needed. Therefore, a single, unified, integrated one-piece antimicrobial dressing with features of complete 360 degree encirclement of catheter lumen at the insertion site has been a need, long-felt but heretofore unmet.

SUMMARY OF THE INVENTION

The present invention provides a dressing having an integral antimicrobial element that is capable of integration into the simplest dressing, such as a single layer TSM (e.g., transparent semipermeable polyurethane film membrane dressing), up to and through multi-layer high functionality dressings with integrated anchoring. The integrated dressing includes an integral antimicrobial material (CHG, silver, or similar) having up to a 7 day dwell and time controlled antimicrobial release, allowing for easy alignment of the integral antimicrobial portion with the catheter and insertion site at the same time that the dressing is applied to a patient's skin. The dressing also may provide a zone of inhibition up to some distance away from the edges of the antimicrobial portion that completely surrounds and reaches the catheter insertion site and completely covers the patient's skin in the region of the antimicrobial material.

More particularly, an integrated antimicrobial dressing in accordance with the present invention includes a transparent film layer having a top side, an opposite bottom side, and an insertion site viewing portion. The bottom side has an adhesive portion and an adhesive-free portion. The adhesive-free portion is disposed within the insertion site viewing portion. An antimicrobial member having a top side and an opposite bottom side is disposed in the insertion site viewing portion. A portion of the antimicrobial member is adhered to the film layer adhesive portion, and a portion of the antimicrobial member is disposed in the adhesive-free portion. The antimicrobial member includes an outer edge and an opening disposed within the outer edge. The opening is disposed in the adhesive-free portion. The antimicrobial member is cooperable with a catheter extending from an insertion site on a patient such that the catheter extends through the opening in the antimicrobial member and site when the dressing is applied to the patient.

The opening in the antimicrobial member may be generally centrally disposed. The opening may be generally circular. The antimicrobial member may include a slit extending from the opening to the outer edge. The slit may be disposed in the adhesive-free portion. Alternatively, the antimicrobial member may include a generally V-shaped slot extending from the opening to the outer edge such that the slot is wider at the outer edge than at the opening. The slot may be disposed in the adhesive-free portion.

Approximately one-third of the antimicrobial member may be adhered to the adhesive portion of the transparent film layer and approximately two-thirds of the antimicrobial member may be disposed in the adhesive-free portion. A portion of the outer edge may be disposed within the adhesive-free portion such that the outer edge is spaced from a boundary of the adhesive-free portion. A gap between the outer edge and the boundary of the adhesive-free portion may be at least 0.0625 to 0.125 of an inch in width.

The antimicrobial member may include at least one of an antimicrobial agent, an antifungal agent, an antiseptic agent, an antibacteriocidal agent, an antiviral agent, and an anticoagulant agent. The adhesive on the transparent film layer bottom side may include at least one of an antimicrobial agent, an antifungal agent, an antiseptic agent, an antibacteriocidal agent, and an antiviral agent. The antimicrobial member may be made of a carrier material impregnated with at least one of an antimicrobial agent, an antifungal agent, an antiseptic agent, an antibacteriocidal agent, an antiviral agent, an anticoagulant agent, and including a slow release binder. The antimicrobial member may include a carrier layer comprising the carrier material, and an adjacent fibrous layer.

A fabric layer having a top side, an opposite bottom side, and an opening therein may be adhered to one of the film layer top side and the film layer bottom side. The opening may define the insertion site viewing portion. An optional absorbent pad may be adhered to said film layer bottom side. The absorbent pad may be generally disposed in or adjacent to the insertion site viewing portion. The absorbent pad may be generally disposed outside of the antimicrobial member. An absorbent pad link member may connect the absorbent pad to the antimicrobial member. An anchor member including a reinforcing structure may be adhered to one of the fabric layer top side and the fabric layer bottom side. The anchor member may be disposed between the fabric layer and the film layer. The anchor member may be disposed outside of the insertion site viewing portion.

A release liner arrangement may be releasably mounted on the transparent film layer bottom side. The release liner may include a first member and a second member. Each of the first member and second member may include a mounted portion mounted on a portion of the transparent film layer and a gripping tab portion folded relative to the mounted portion. The release liner further may include a third member. The third member may be mounted on a portion of the transparent film layer intermediate the first and second member, and the third member may extend over the gripping tab portions of the first and second members. The third member may be releasable from the transparent film layer without tampering with the first and second members. Each of the first and second members may be releasable from the transparent film layer without tampering with the other of the first and second members.

These and other features and advantages of the invention will be more fully understood from the following detailed description of the invention taken together with the accompanying drawings.

BRIEF DESCRIPTION OF THE DRAWINGS

In the drawings:

FIG. 18 is a perspective view of an alternative embodiment of a dressing having integral antimicrobial in accordance with the invention;

FIG. 19 is a cross-sectional view taken along the line 19-19 in FIG. 18;

FIG. 20 is a perspective view of an alternative embodiment of a dressing having integral antimicrobial in accordance with the invention;

DETAILED DESCRIPTION OF THE INVENTION

Figure 1:
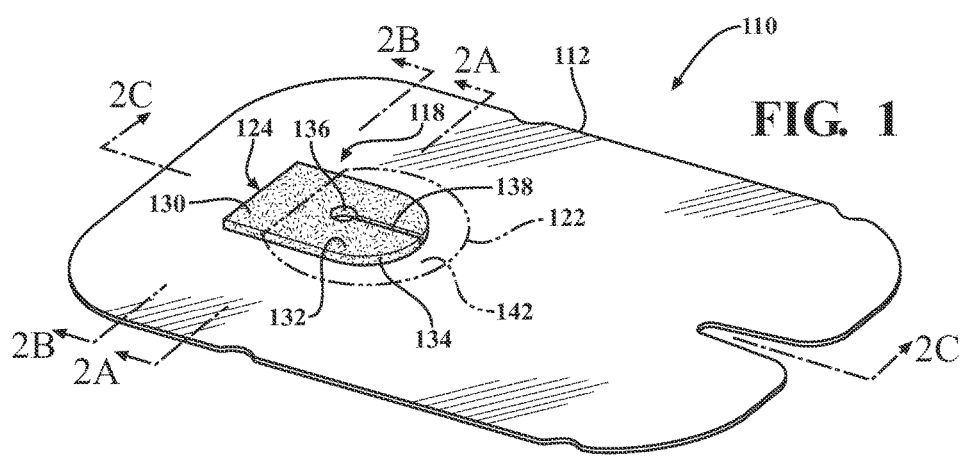
FIG. 1 is a perspective view of an integrated antimicrobial dressing in accordance with the present invention.
Figure 2A:
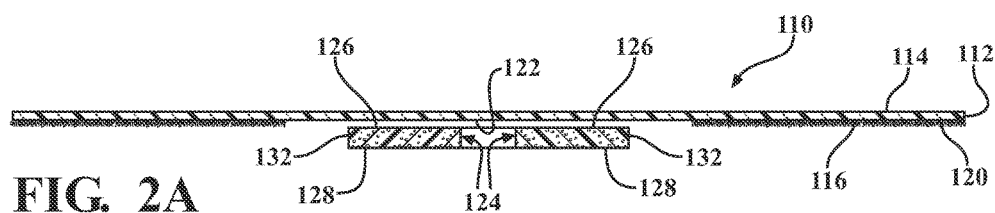
FIG. 2A is a cross-sectional view taken along the line 2A-2A in FIG. 1.
Figure 2B:
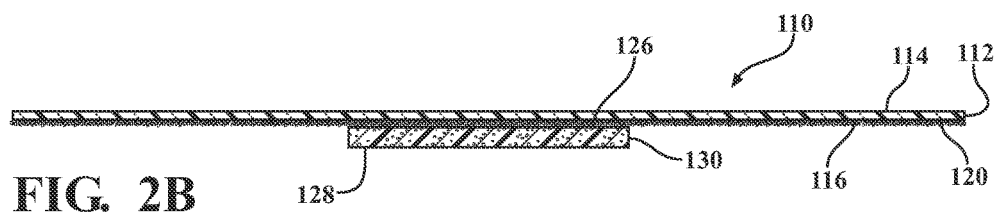
FIG. 2B is a cross-sectional view taken along the line 2B-2B in FIG. 1.
Figure 2C:
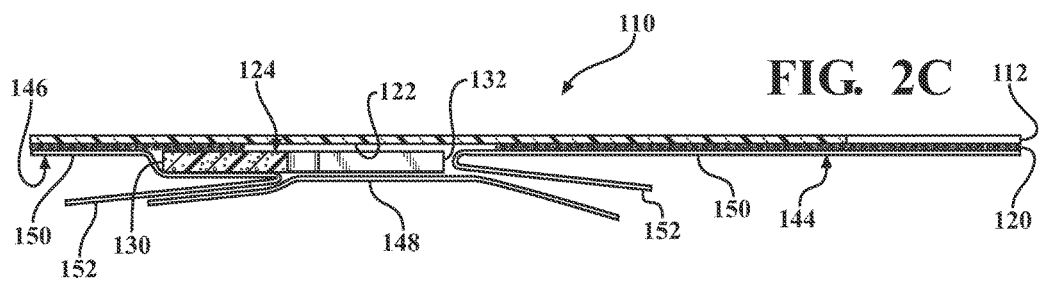
FIG. 2C is a cross-sectional view taken along the line 2C-2C in FIG. 1.

Referring now to the drawings in detail, numeral 110 generally indicates a dressing having an integral antimicrobial. The dressing provides a zone of inhibition directly under and up to some distance away from any of the edges of the antimicrobial portion that completely surrounds and reaches the catheter insertion site and completely covers the patient's skin in the region of the antimicrobial material.

Turning to FIGS. 1 and 2A through 2C, an integrated antimicrobial dressing 110 in accordance with the invention includes a first layer 112 which may be a transparent semipermeable film layer such as a polyurethane film or similar. The first layer 112 alternatively may be a fabric layer such as a woven or non-woven fabric. The transparent film layer 112 has a top side 114, an opposite bottom side 116, and an insertion site viewing portion 118 within the boundaries of the film layer. The film layer bottom side 116 includes an adhesive portion 120 having an adhesive thereon and an adhesive-free portion 122 that is generally free of adhesive. The adhesive-free portion 122 is disposed within the insertion site viewing portion 118.

Figure 3:
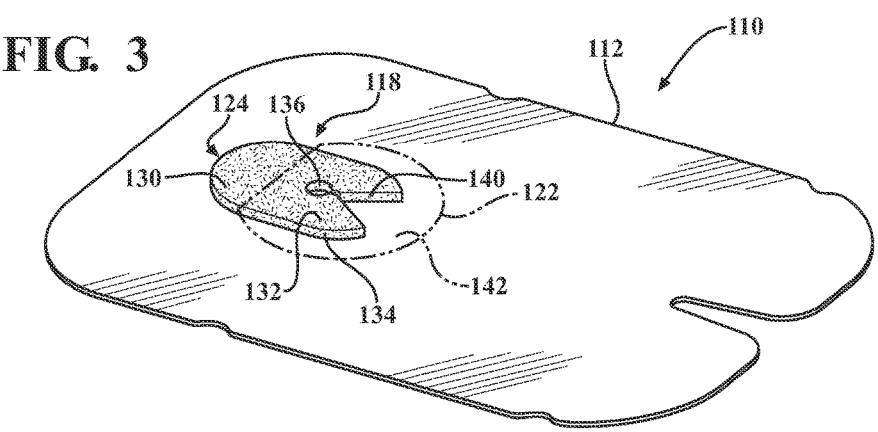
FIG. 3 is a perspective view of an alternative embodiment of an integrated antimicrobial dressing in accordance with the present invention.

An antimicrobial member 124 having a top side 126 and an opposite bottom side 128 is disposed in the insertion site viewing portion 118. A portion 130 of the antimicrobial member 124 is adhered to the film layer bottom side 116 in the insertion site viewing portion 118. Another portion 132 of the antimicrobial member 124 is disposed in the adhesive-free portion 122. Thus, the portion 130 of the antimicrobial member 124 is mounted on the adhesive 120 bottom surface 116 of the film layer 112 while the portion 132 is placed on/adjacent the adhesive-free portion 122 of the film layer 112 in a vertical direction (i.e., looking at the dressing 110 from top to bottom). The portion 130 and the portion 132 are mutually exclusive and together define the entire antimicrobial member 124. The portion 130 may form approximately one-third of the antimicrobial member 124 and the portion 132 may form the other approximately two-thirds of the antimicrobial member. Hence, approximately two-thirds of the antimicrobial member 124 may be disposed in the adhesive-free portion 122. The antimicrobial member 124 includes an outer edge 134 and an opening 136 disposed within the boundaries of the outer edge and extending through the antimicrobial member from the top side 126 to the bottom side 128. The opening is disposed in the portion 132 of the antimicrobial member 124 that is in the adhesive-free portion 122 of the film layer 112. The opening 136 may be generally centrally disposed within/inwardly from the boundaries of the antimicrobial member 124. The opening 136 may be generally circular/cylindrical. A slit 138 extends from the opening 136 outwardly to the outer edge 134 of the antimicrobial member 124. Alternatively but similarly, as shown in FIG. 3 the antimicrobial member 124 may include a generally V-shaped tapered slot 140 extending from the opening 136 to the outer edge 134 of the antimicrobial member such that the slot 140 is wider at the outer edge than at the opening (i.e., the taper of the slot opens outwardly). The slit 138 or slot 140 may be disposed in the non-adhered portion 132 of the antimicrobial member 124 and thus in the adhesive-free portion 122 of the film layer 122 (i.e., adjacent in a vertical direction). A portion of the outer edge 134 of the antimicrobial member 124 may be disposed within the adhesive-free portion 122 such that the outer edge is spaced from a boundary of the adhesive-free portion. A gap 142 between the outer edge 134 and the boundary of the adhesive-free portion 122 may be at least 0.0625 to 0.125 of an inch in width, although the exact width of the gap may vary so long as the slit 138 or slot 140 is not "locked closed" by adhesive on the film layer 122 above. The amount of free space between the outer edge 134 of the antimicrobial member 124 and the boundary of the adhesive-free portion 122 may be varied to create various functionality. For example, if the gap 142 is very small the slit 138 has a higher tendency to remain "closed" in actual use of the dressing 110, but it may also be more difficult to "open" at dressing application when it is necessary to place the dressing 110 and its associated lumen encircling antimicrobial member 124 around a larger lumen or nose of a catheter hub, especially if the catheter is a large diameter or multi-lumen catheter.

The antimicrobial member 124 is not limited to any particular shape and may be round, oval, elliptical, pear-shaped, bullet-shaped, clam shell-shaped, truncated, or any other suitable shape or size. For very small diameter catheters, hole 136 may be simply a continuation of slit 138. The boundary of the adhesive-free portion 122 may generally mimic and correspond in shape to the shape of the portion 132 of the antimicrobial member 124 that lies in the adhesive-free portion 122, albeit the adhesive-free portion 122 is wider/larger than the antimicrobial member 124 so that the slit 138 can flex open, to encircle and then close back around and under the lumen.

The antimicrobial member bottom side 128 may include an adhesive thereon, and the antimicrobial member bottom side may include both an adhesive portion and an adhesive-free portion adjacent the slit 138 or slot 140. Alternatively, the antimicrobial member bottom side may have no adhesive thereon. The optional adhesive portion reduces shifting of the antimicrobial member 124 on irregularly shaped patient body features about the insertion site. The adhesive on the adhesive portion may be continuous, or it may be interrupted, discontinuous, patterned, dotted, island shaped, or may have round or other shaped adhesive voids to facilitate agent leach out from the antimicrobial member to the skin, such that the adhesive is preferably breathable (i.e., permeable), and may not interfere with, impede on, or retard the slow release of antimicrobial agent (see below) from the antimicrobial member 124 through the adhesive layer. The adhesive free portion facilitates placement of the antimicrobial member 124 over and around an insertion site and/or catheter lumen as the dressing is being applied to the patient at the insertion site.

The antimicrobial member 124 may be made of a foam layer such as a hydrophilic polyurethane foam or similar that has absorbency. Alternatively, the antimicrobial member 124 may be partially or entirely made from viscose, gel(s), hydrogel(s), hydrocolloid(s), fabric, cellulose, rayon, or similar as a carrier material for the antimicrobial agent(s). The material of the antimicrobial member 124 is not particularly limited so long as it is capable of carrying (e.g., binding) and releasing (e.g., slow-releasing) an antimicrobial and/or antifungal or antiviral agent.

The antimicrobial member 124 may include an active antimicrobial agent and/or an antifungal agent and/or an antiseptic agent including but not limited to chlorhexidine gluconate (CHG), silver compounds such as silver alginate, silver ionic colloids or similar, Microban® triclosan, minocycline-rifampin, silver-platinum-carbon, chlorhexadine-silver-sulfadiazine, or others. For example, the antimicrobial member 124 may be a foam material (e.g., polyurethane foam or similar) impregnated with CHG including slow release binders and slow release properties. Alternatively, the antimicrobial member 124 may be a gel material that includes CHG, although the antimicrobial member may be made of any material capable of carrying and releasing an active antimicrobial agent. When the dressing is applied on a patient, the antimicrobial member delivers the active agent for a period of generally from time zero (time of application on patient) to up to at least seven to ten days. Also, the antimicrobial member (foam, gel, pad, etc.) may include binders or mediator compounds and may also include agents that facilitate controlled release and other functionality related to biological release, biocompatibility, non-toxicity, anticoagulants, microbial kill rate, manufacturability, shelf-life stability, and an optimized zone of inhibition (see below). The slow release binders and/or mediator compounds facilitate controlled emission of antimicrobial agent to the skin over a desired seven to ten day period. The adhesive of the adhesive portion 134 on the bottom side 128 of the antimicrobial member as well as the adhesive on the adhesive portion 120 of the film layer 112 also may include at least one of an antimicrobial agent, an antifungal agent, and an antiseptic agent. The agents in the antimicrobial member, the adhesive, and the film layer may be the same or different.

The integrated antimicrobial dressing 110 may also include a single sheet release liner, or to facilitate easy opening of the slit 138 or slot 140, and encirclement by hole 136, and reclosure of slit 138 or slot 140, a system of release liners releasably mounted on the transparent film layer bottom side 116. The system of release liners may include a first member 144, a second member 146, and a third member 148. The first member 144 and the second member 146 each include a mounted portion 150 mounted on a portion of the transparent film layer 112 and a gripping tab portion 152 folded over the mounted portion 150. The third member 148 is mounted on a portion of the transparent film layer 112 intermediate the portions on which the first and second members 144, 146 are mounted, and the third member 148 extends over the gripping tab portions 152 of the first and second members 144, 146. The third member 148 is releasable from the transparent film layer 112 without tampering with the first and second members 144, 146, and each of the first and second members 144, 146 is releasable from the transparent film layer 112 without tampering with the other member. Alternatively, the release liner system may include only two release liner members, although in this arrangement the position of a boundary between the two members becomes important so that removal of the first of the two liners exposes a desired amount and portion of the transparent film layer and antimicrobial member during application of the dressing on a patient, as is discussed in more detail below.

In use, the dressing 110 is disposed over a catheter insertion site such that the insertion site and catheter lumen extending from the insertion site are disposed within or above the slit 138 or V-shaped slot 140 of the antimicrobial member 124. Thus, the insertion site and catheter lumen are entirely surrounded by the antimicrobial member 124, and the antimicrobial member forms a barrier against colonization and infection of the insertion site. Microorganisms may be found on a patient's skin, the subcutaneous catheter insertion tract, or in the patient's blood and/or may be introduced via the catheter or a medical clinician's hands. Microorganism colonization at or around a patient catheter insertion site can undesirably lead to catheter related blood stream infection ("CRBSI"), a serious prognosis that typically costs in the range of $10,000 to $40,000 to treat and potentially can lead to death.

The antimicrobial member 124 may have a low profile, i.e. a low height of, for example, approximately 1/16 of an inch. However, the antimicrobial member is not limited to a specific profile, and may have a height of closer to 1/4 of an inch as shown in the embodiments below.

Figure 4:
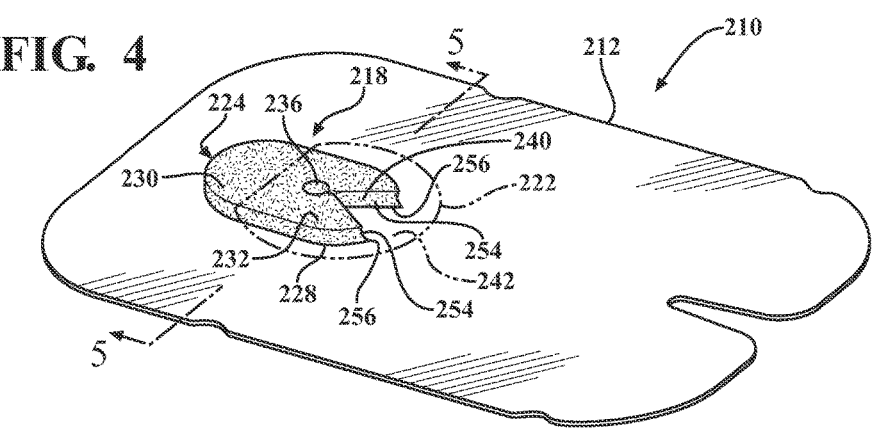
FIG. 4 is a perspective view of an alternative embodiment of a dressing having integral antimicrobial in accordance with the invention.
Figure 5:
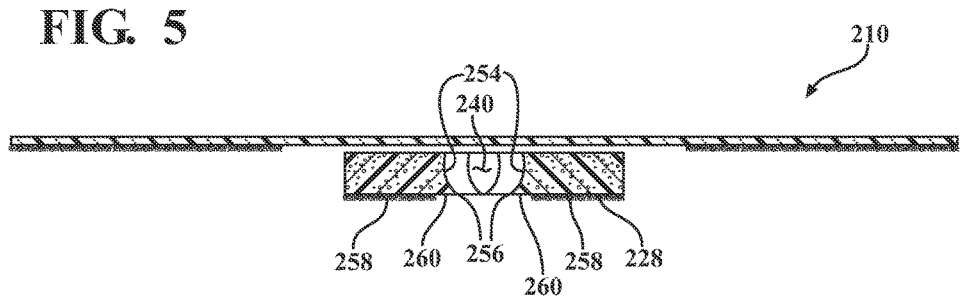
FIG. 5 is a cross-sectional view taken along the line 5-5 in FIG. 4.

In the following embodiments, like reference numbers represent similar parts as those of the first embodiment 110. In an embodiment 210 shown in FIGS. 4 and 5, the antimicrobial member 224 may include a curved sidewall 254 adjacent to and facing the V-shaped slot 240 (or the slit). For instance, the sidewall 254 may have a semi-circular cross-section. The curved sidewalls 254 aide in retaining a catheter lumen (and medical tubing in general) in the slot 240. The antimicrobial member 210 also may include a blade 256 extending along the bottom side 228 from the curved sidewall 254 inwardly into the slot 240. The blades 256 effectively reduce the width of the slot 240 close to a patient's skin, allowing the gap (width) between the sidewalls 254 to be smaller adjacent the patient's skin, which is important for maintaining antimicrobial coverage in the area within the slot. The antimicrobial member bottom side 228 may include both an adhesive portion 258 and an adhesive free portion 260 adjacent the slot 240 that generally corresponds with the blades 256, i.e., the blades do not have any adhesive thereon. This configuration also helps to keep the catheter lumen from pressing too far into a patient's skin, which can reduce the antimicrobial's crawl distance in the compressed area between the top of the skin and the catheter bottom.

Figure 6:
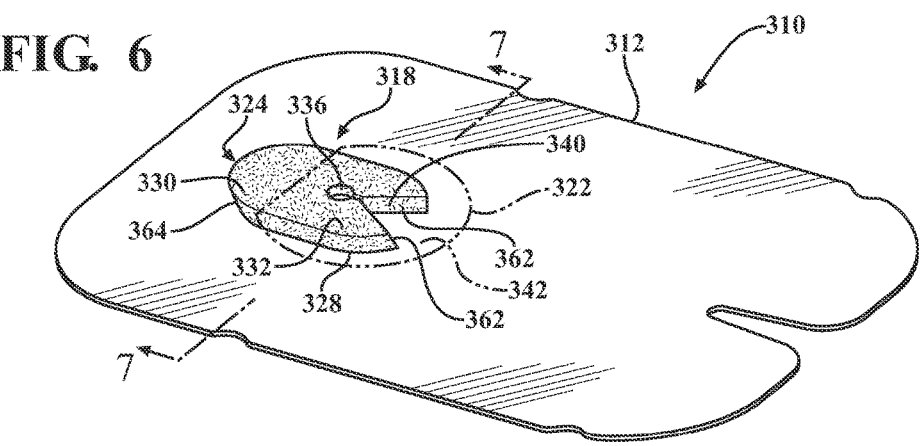
FIG. 6 is a perspective view of an alternative embodiment of a dressing having integral antimicrobial in accordance with the invention.
Figure 7:
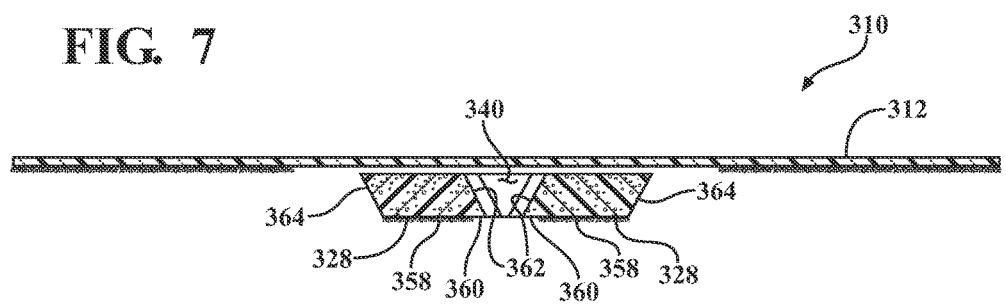
FIG. 7 is a cross-sectional view taken along the line 7-7 in FIG. 6.

In another embodiment 310 shown in FIGS. 6 and 7, the V-shaped slot 340 (or the slit) of the antimicrobial member 324 may include a sloped inner sidewall 362 such that the slot 340 is tapered towards the antimicrobial member bottom side 328. The antimicrobial member 324 may also include a sloped outer sidewall 364 that is tapered inwardly towards the center of the member 324 in a direction from the film layer 312 to the bottom side 328 of the member 324. The sloped sidewalls 362, 364 reduce tenting of the film layer 312 over a patient's skin when the dressing is applied to a patient's skin. In other words, the sloped sidewalls 362, 364 reduce the amount of open space between the patient's skin and the dressing and/or the height of the dressing over the patient's skin. The sloped sidewalls 362, 364 also cause the film layer to pivot the antimicrobial member 324 such that the width of the slot 340 is reduced, i.e., the gap distance between the edges of the slot 340 is reduced when the dressing is applied to a patient's skin, and the slot 340 can be pivoted open by bending the dressing prior to applying it to a patient's skin. The antimicrobial member bottom side 328 may include both an adhesive portion 358 and an adhesive free portion 360 adjacent the slot. This configuration also helps to keep the catheter from pressing too hard against the skin, which reduces suppression of the coverage of the antimicrobial member 324.

Figure 8:
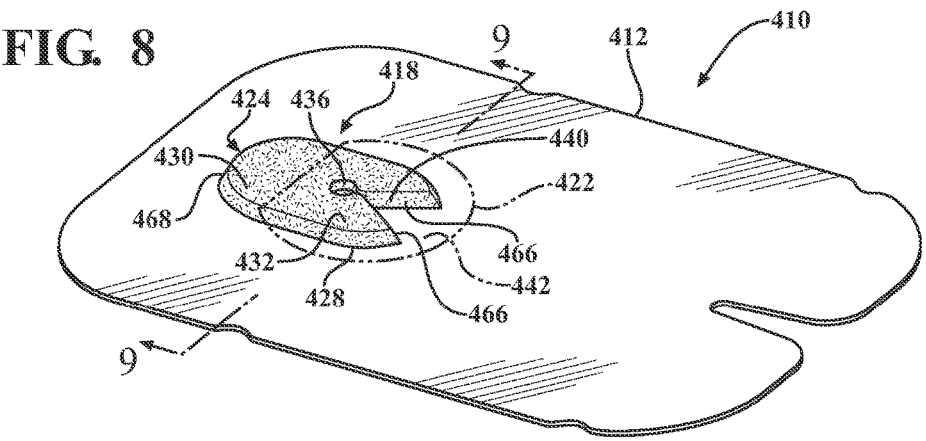
FIG. 8 is a perspective view of an alternative embodiment of a dressing having integral antimicrobial in accordance with the invention.
Figure 9:
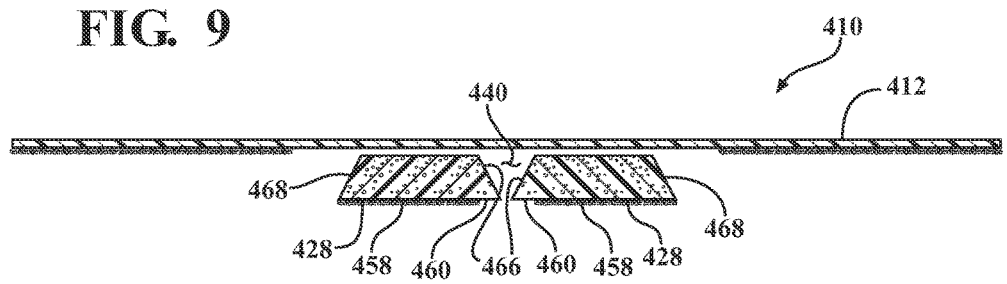
FIG. 9 is a cross-sectional view taken along the line 9-9 in FIG. 8.

In another embodiment 410 shown in FIGS. 8 and 9, the V-shaped slot 440 (or the slit) of the antimicrobial member 424 may include a sloped inner sidewall 466 such that the slot 440 is tapered towards the antimicrobial member bottom side 428. The antimicrobial member 424 may also include a sloped outer sidewall 468 that is tapered outwardly away from the center of the member 424 in a direction from the film layer 412 to the bottom side 428 of the member 424. As in the embodiment above, the sloped sidewalls 466, 468 reduce tenting of the film layer 412 and allow the slot to be pivoted open and closed. The antimicrobial member bottom side 428 may include both an adhesive portion 458 and an adhesive free portion 460 adjacent the slot.

Figure 10:
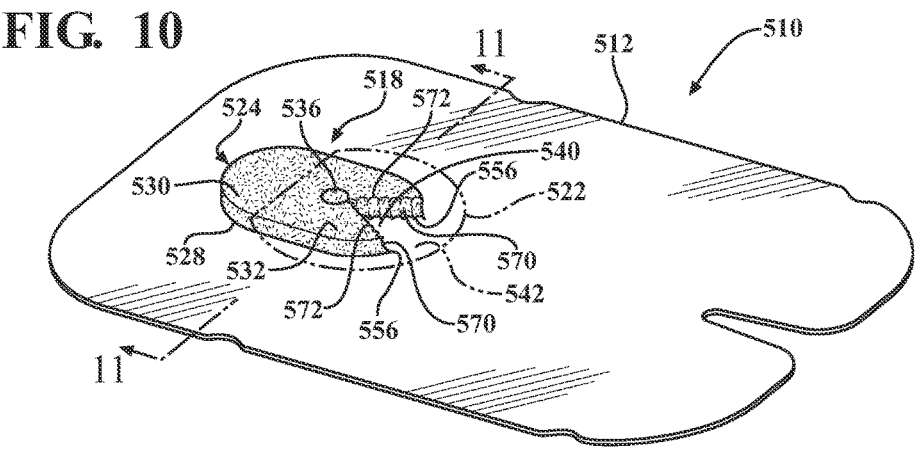
FIG. 10 is a perspective view of an alternative embodiment of a dressing having integral antimicrobial in accordance with the invention.
Figure 11:
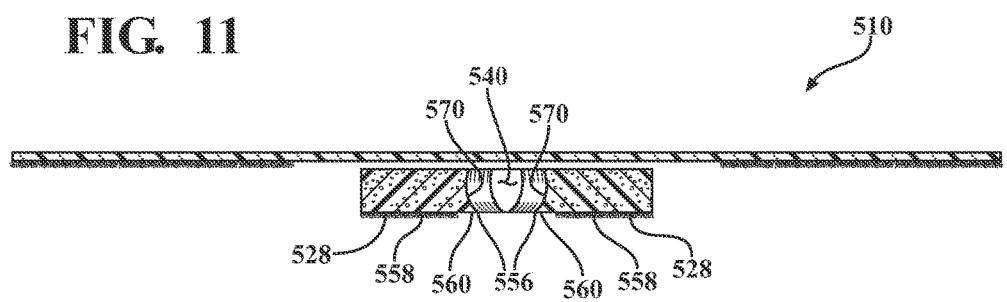
FIG. 11 is a cross-sectional view taken along the line 11-11 in FIG. 10.

In another embodiment 510 shown in FIGS. 10 and 11, the V-shaped slot 540 (or the slit) of the antimicrobial member 524 may include a sidewall 570 adjacent to and facing the slot 540 that has a scalloped surface including scallops 572 vertically disposed along the length of the slot 540. The scallops 572 aide in snugly securing in a conforming fashion, a catheter or other medical tubing in the slot 540 around the vertical portion as it emanates from the insertion site after being bent over ninety degrees parallel to the skin. The lower edges of the slot 540 also may include a blade 556 extending along the bottom side 528 from the scalloped sidewall 570 inwardly into the slot 540. Any scallop encircles the vertical portion of lumen, allowing the blade to nestle up tightly under the horizontal portion of lumen. The antimicrobial member bottom side 528 may include both an adhesive portion 558 and an adhesive free portion 560 adjacent the slot 540 that generally corresponds with the blades 556, i.e., the blades do not have any adhesive thereon, to facilitate closure around the vertical and horizontal portions of the catheter emanating from the insertion site, to reach as far under the catheter as possible.

Figure 12:
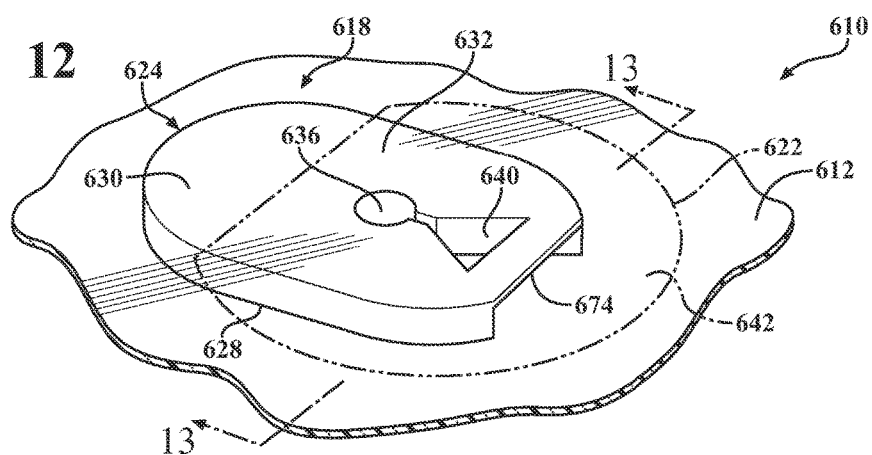
FIG. 12 is a perspective view of an alternative embodiment of a dressing having integral antimicrobial in accordance with the invention.
Figure 13:
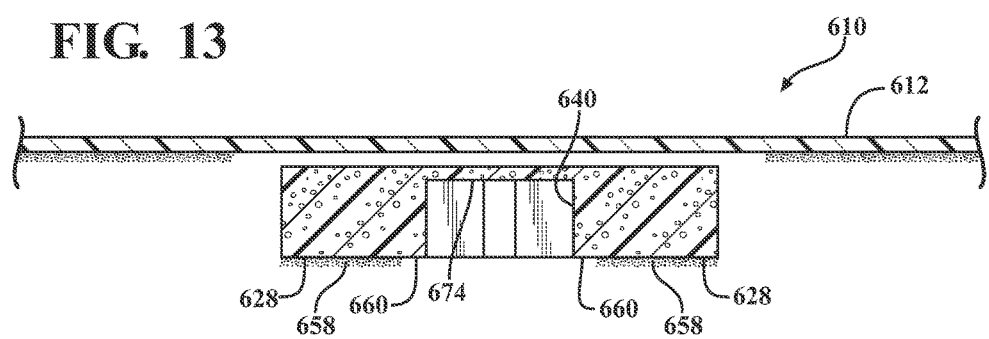
FIG. 13 is a cross-sectional view taken along the line 13-13 in FIG. 12.

In another embodiment 610 shown in FIGS. 12 and 13, the antimicrobial member 624 may include a cross-over tie 674 connecting the two sides of the V-shaped slot 640 (or the slit). The tie 674 may have a height that is less than the height of the antimicrobial member 624, and the tie 674 may be disposed generally adjacent to the film layer 612. The tie 674 stabilizes the antimicrobial member 624 and aides in manufacturing and in maintaining a generally stable disposition between the sides of the slot 640. The tie 674 also prevents against a catheter or other medical tubing pushing the antimicrobial member 624 and/or the film layer 612 up and away from a patient's skin in an area in which the antimicrobial member crosses or lies over the catheter. The tie 674 also allows the antimicrobial member 624 to cross over a catheter without pushing the antimicrobial member up and away from a patient's skin. This is important when the conditions are such that, when the dressing is applied to a patient, the cross-over tie lands on or near to a location within about one-half to three-quarters of an inch from the insertion site, which may occur, for example, when the catheter French OD size is generally large (i.e., 7 FR and up). In such a case, the bottom side 628 of the antimicrobial member 624 (and the rest of the dressing layer(s), e.g. the film layer) may become tented away from the skin at and around the insertion site, decreasing the antimicrobial reach of the antimicrobial member to a level that may less than effectively inhibit colonization at the main target, which is an area of approximately one-half to one inch in radius around the insertion site. However, the cross-over tie 674 defines a channel between the dressing and a patient's skin through which the catheter lumen can pass without pushing the dressing away from the patient's skin. The antimicrobial member bottom side 628 may also include both an adhesive portion 658 and an adhesive free portion 660 adjacent the slot 640.

Figure 14:
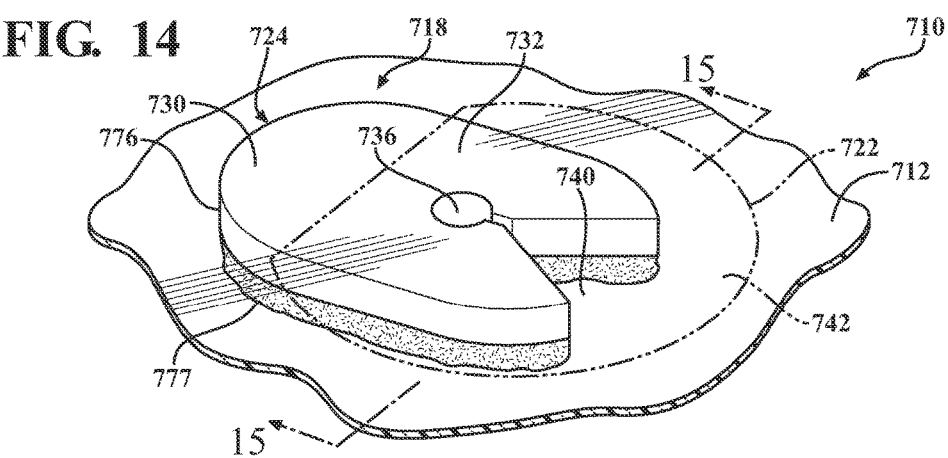
FIG. 14 is a perspective view of an alternative embodiment of a dressing having integral antimicrobial in accordance with the invention.
Figure 15:
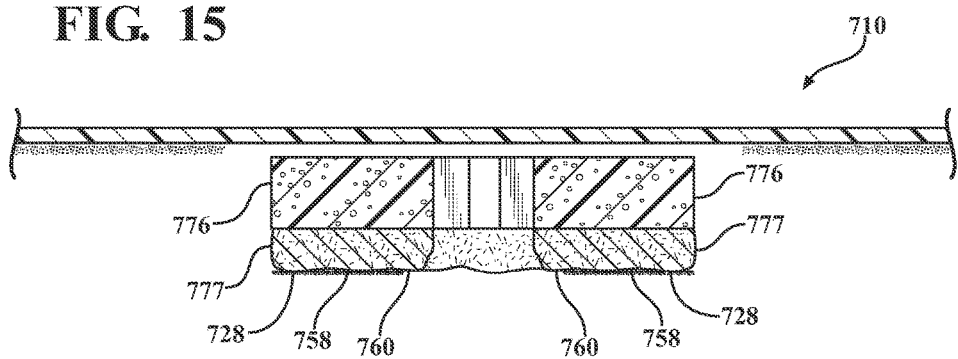
FIG. 15 is a cross-sectional view taken along the line 15-15 in FIG. 14.

In another embodiment 710 shown in FIGS. 14 and 15, the antimicrobial member 724 may be a dual-density member including a foam layer 776 and an adjacent cotton layer 777 disposed underneath the foam layer and defining the bottom side 728 of the antimicrobial member. The antimicrobial member bottom side 728 may also include both an adhesive portion 758 and an adhesive free portion 760 adjacent the V-shaped slot 740 (or the slit).

Although the axis of the antimicrobial member (i.e., an axis generally passing through the slit or the V-shaped slot) is shown as being aligned parallel with a main axis of the dressing, the axis of the antimicrobial member may be rotated 10 to 90 degrees relative to the dressing main axis.

It should be understood that an antimicrobial member in accordance with the present invention may have any combination of the structures and features described above.

The dressing having the integral antimicrobial allows for transparent viewing, including over and through the slot, of the insertion site through the clear transparent film layer during the dressing installation and during the dressing dwell time on a patient's skin. The transparent view of the insertion site allows clinicians to check for blood, exudate, redness, swelling, eschar, and other patient wound issues at the insertion site while the dressing is in place. In contrast, conventional antimicrobial, separate piece dressings/devices distort, tint, color, or totally block the view of the insertion site.

Figure 16:
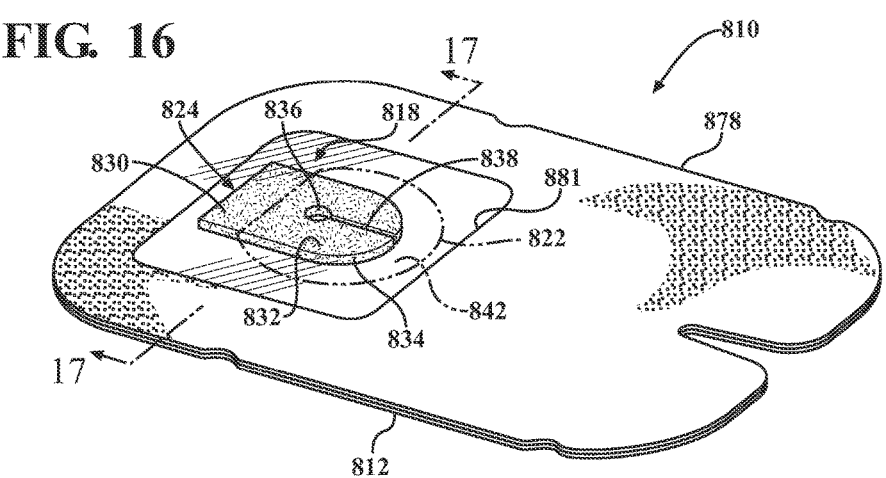
FIG. 16 is a perspective view of an alternative embodiment of a dressing having integral antimicrobial in accordance with the invention.
Figure 17:
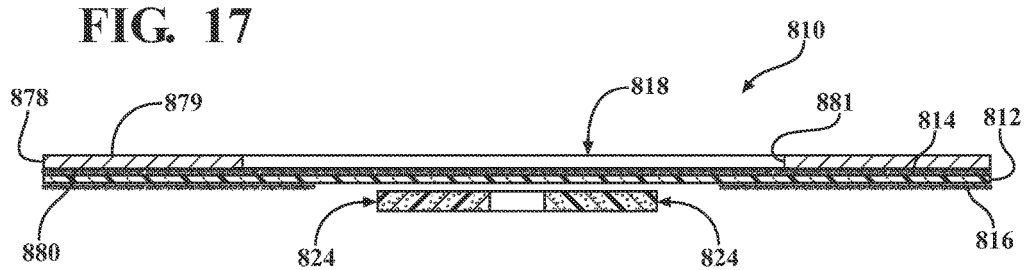
FIG. 17 is a cross-sectional view taken along the line 17-17 in FIG. 16.

Turning to FIGS. 16 and 17, an integrated antimicrobial dressing 810 in accordance with the present invention may further include a fabric layer 878 having a top side 879, an opposite bottom side 880, and an opening 881 therein defining the insertion site viewing portion 818. The fabric layer may be adhered to one of the film layer 812 top side 814 or the film layer bottom side 816. The film layer 812 generally closes the opening 881 in the fabric layer 878, and the film layer is adhered around the opening such that the film layer extends beyond the edge of the opening. The fabric layer 878 may be any suitable woven or non-woven fabric material. The dressing 810 includes an antimicrobial member 824 having any combination of the features described above.

Optionally, as shown in FIGS. 18 and 19 the dressing 910 may also include an absorbent pad 982 adhered to the film layer 912 bottom side 916. The absorbent pad 982 may be generally disposed in or adjacent to the insertion site viewing portion 918. For example, the absorbent pad 982 may generally circumscribe the insertion site viewing portion and/or the absorbent pad may generally lie along the perimeter of the opening 981 in the fabric layer 978, if present. The absorbent pad 982 also may be generally disposed outside of the antimicrobial member 924 such that the absorbent pad partially or entirely surrounds the antimicrobial member. The absorbent pad 982 absorbs excess fluids, exudate, etc. that is not absorbed by the antimicrobial member 924. The antimicrobial member 924 may have any combination of the features described above. Further, a link member 984 (shown in phantom line in FIG. 18) that is made of an absorbent material or similar may form an isthmus that connects the absorbent pad 982 to the antimicrobial member 924. For example, the dressing may include two link members 984, and each link member may connect the absorbent pad 982 to one of the antimicrobial member portions. The link member(s) 984 increase the absorbent capacity of the dressing and provide for wicking of fluid, exudates, etc. to the absorbent pad 982 away from the antimicrobial member 924 and the insertion site.

Figure 21:
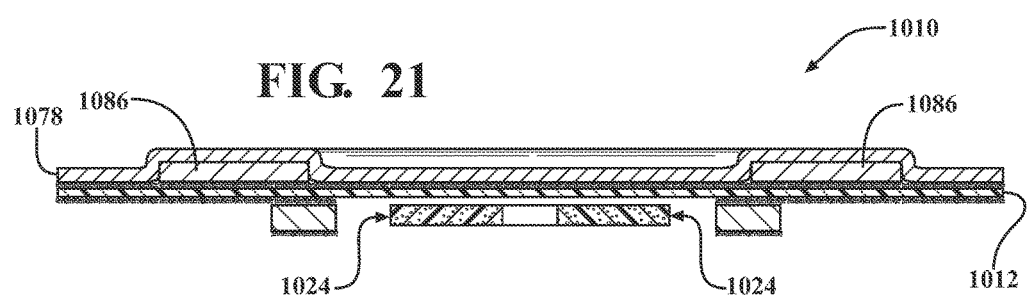
FIG. 21 is a cross-sectional view taken along the line 21-21 in FIG. 20.
Figure 22:
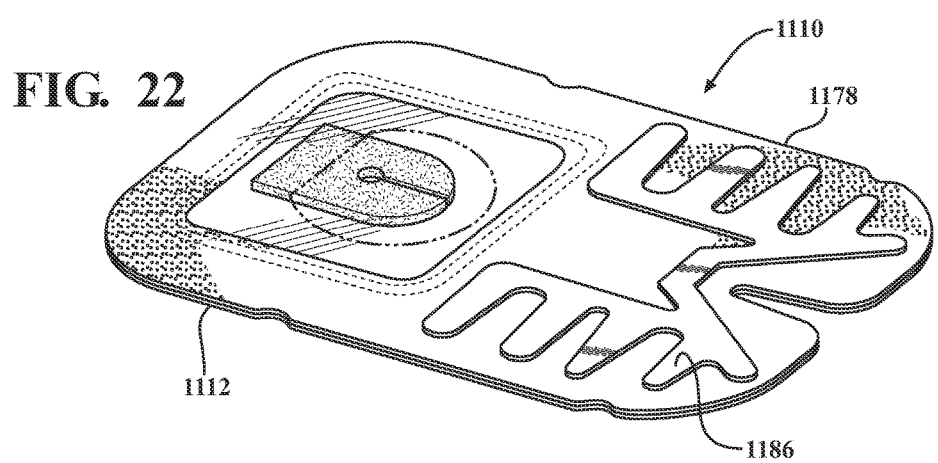
FIG. 22 is a perspective view of an alternative embodiment of a dressing having integral antimicrobial in accordance with the invention.

In another embodiment shown in FIGS. 20 and 21, an integrated antimicrobial dressing 1010 in accordance with the present invention may further include an integral anchor member 1086 including a reinforcing structure that strengthens the dressing and resists tugging and pull forces from peeling the dressing away from a patient's skin once the dressing has been applied. The anchor member 1086 is adhered to one of the fabric layer top side or the fabric layer bottom side. For example, the anchor member 1086 may be disposed between the fabric layer 1078 and the film layer 1012. Alternatively, as shown in FIG. 22, in an embodiment 1110 the anchor member 1186 may be disposed on top of the fabric layer 1178 which is on top of film layer 1112. The anchor member is also typically disposed outside of the insertion site viewing portion 1018. The dressing 1010 includes an antimicrobial member 1024 having any combination of the features described above.

It should be understood that an integrated antimicrobial dressing in accordance with the present invention may have any combination of the stack layers described above.

Figure 23:
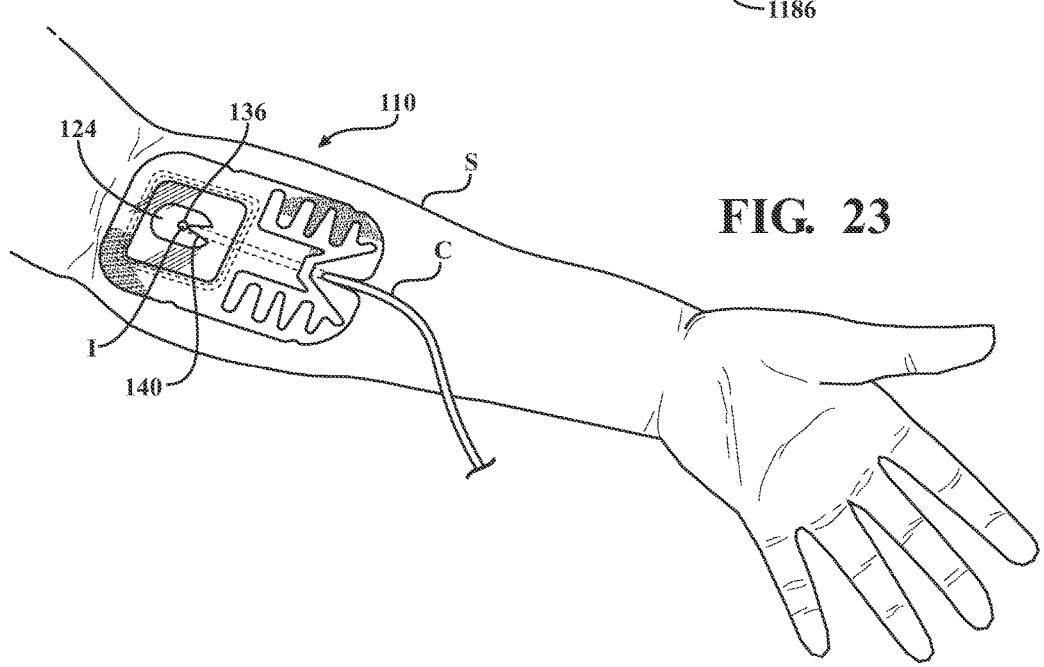
FIG. 23 is an environmental view of the dressing having integral antimicrobial applied to a patient's skin.

Turning to FIG. 23, the dressing 110 may be applied to a patient's skin S around a catheter insertion site I. The dressing 110 specifically may be positioned in a manner such that the insertion site I generally lies in the opening 136 adjacent the V-shaped slot 140. The catheter C extending from the catheter insertion site I also lies in and extends out of the slot 140 such that the catheter insertion site I and catheter C are surrounded by the antimicrobial member 124 in the general vicinity of the antimicrobial member. Thus, the antimicrobial member 124 forms a barrier against colonization and infection of the insertion site I.

With reference again to FIGS. 1 and 2, to apply the dressing 110, the first step is to remove the third member 148 of the release liner. This exposes a middle portion of the dressing 110 including the non-adhered portion 132 of the antimicrobial member 124 in the adhesive-free portion of the film layer bottom side 116. Next, the long two-thirds of the dressing 110 (generally corresponding to the portion on which the first release liner member 144 is mounted) is folded all the way down to the opening 136 at the end of the slit 138 (or V-shaped slot). In other words, the long two-thirds of the dressing is folded over the short one-third of the dressing generally along a line separating the non-adhered portion 132 of the antimicrobial member 124 from the adhered portion 130 of the antimicrobial member. The slit 138 and opening 136 are now exposed as the non-adhered portion 132 of the antimicrobial member 124 extends away from the folded dressing. The user then grasps the dressing 110 with one hand, placing the thumb on the topside of the exposed adhesive-free portion 122 and the other two to four fingers on the underside of the portion 152 of the second release liner member 146. Next, the user should lift the catheter slightly away from the patient's skin using his/her free hand, and should simultaneously slide the exposed slit 138 (or V-shaped slot) past the catheter lumen at the insertion site unit the lumen is fully disposed in the opening 136 of the antimicrobial member 124. Maintaining the position of the antimicrobial member 124 closed and around the catheter lumen, the user then gently shifts his/her four fingers from under the release liner second member 146 to the top side 114 of the viewing portion 118 window. The user then flips the long two-thirds portion of the dressing 110 back to a flat disposition so that the dressing is disposed over the antimicrobial member 124, the catheter hub, and pigtails extending from the hub. Optionally, a 20 to 30 degree turn of the dressing 110 can be made at this point, in order to lay the catheter lumen on top of the antimicrobial member 124 (i.e., next to the slit 138 or V-shaped slot). From the top side 114 of the dressing 110, the user squeezes the film layer 112 at the viewing portion 118 with a thumb and index finger to press the slit 138 (or V-shaped slot) closed, while simultaneously tacking some of the exposed adhesive on the film layer bottom side 116 onto the patient's skin on each side of the catheter lumen and hub. Next, the user removes the release liner first member 144 from the film layer bottom side 116 (gradually or all at once) to expose the adhesive on the long two-thirds portion. The exposed adhesive bottom side of the film layer is then pressed against the patient's skin to adhere this portion of the dressing. Finally, the short, remaining second release liner member 146 at the far end of the insertion site viewing portion 118 is removed from the film layer bottom side 116 (gradually or all at once) to expose the adhesive on the bottom side. This portion of the dressing 110 is pressed against the patient's skin to adhere the rest of the dressing 110 to the patient.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A dressing comprising:
   a foldable transparent film layer having a top side, an opposite bottom side, and an insertion site viewing portion, said bottom side having an adhesive portion and an adhesive-free portion, said adhesive-free portion being disposed within said insertion site viewing portion; and
   an antimicrobial member having a top side and an opposite bottom side, said antimicrobial member being disposed beneath the transparent film layer in said insertion site viewing portion and inboard of an outer periphery of the transparent film layer, a portion of said antimicrobial member being adhered to said film layer adhesive portion;
   said antimicrobial member defined by an outer edge and having one of a slot and a slit defined by an end portion, wherein the slot or slit extends from a portion of the outer edge that is portioned inboard of the outer periphery of the transparent film layer, such that the end portion is positioned inboard of said outer edge;
   wherein said antimicrobial member is cooperable with a catheter extending from an insertion site on a patient such that said catheter extends through said slot or slit in said antimicrobial member and said antimicrobial member surrounds said insertion site when said dressing is applied to said patient.

2. The dressing of claim 1, wherein said end portion of said slot or slit in said antimicrobial member is generally centrally disposed.

3. The dressing of claim 1, wherein said end portion of said slot or slit is configured as a generally circular opening.

4. The dressing of claim 1, wherein said slot or slit is disposed in said adhesive-free portion.

5. The dressing of claim 1, wherein said slot of said antimicrobial member is defined as a generally V-shaped slot extending from said end portion of said slot to said outer edge such that said slot is wider at said outer edge than at said end portion.

6. The dressing of claim 5, wherein said slot is disposed in said adhesive-free portion.

7. The dressing of claim 1, wherein approximately one-third of said antimicrobial member is adhered to said adhesive portion of said transparent film layer and approximately two-thirds of said antimicrobial member is disposed in said adhesive-free portion.

8. The dressing of claim 1, wherein an outermost portion of said outer edge of said antimicrobial member is disposed within said adhesive-free portion such that said outer edge is spaced from a boundary of said adhesive-free portion.

9. The dressing of claim 1, wherein said antimicrobial member includes at least one of an antimicrobial agent, an antifungal agent, an antiseptic agent, an antibacteriocidal agent, an antiviral agent, and an anticoagulant agent.

10. The dressing of claim 1, wherein said adhesive portion on said transparent film layer bottom side includes at least one of an antimicrobial agent, an antifungal agent, an antiseptic agent, an antibacteriocidal agent, and an antiviral agent.

11. The dressing of claim 1, wherein said antimicrobial member is made of a carrier material impregnated with at least one of an antimicrobial agent, an antifungal agent, an antiseptic agent, an antibacteriocidal agent, and an antiviral agent, and including a slow release binder.

12. The dressing of claim 11, wherein said antimicrobial member includes a carrier layer comprising said carrier material, and an adjacent fibrous layer.

13. The dressing of claim 1, including a fabric layer having a top side, an opposite bottom side, and an opening therein;
    said fabric layer being adhered to one of said film layer top side and said film layer bottom side, and said opening defining said insertion site viewing portion.

14. The dressing of claim 13, including an anchor member including a reinforcing structure, said anchor member being adhered to one of said fabric layer top side and said fabric layer bottom side.

15. The dressing of claim 14, wherein said anchor member is disposed between said fabric layer and said film layer.

16. The dressing of claim 14, wherein said anchor member is disposed outside of said insertion site viewing portion.

17. The dressing of claim 13, including an absorbent pad adhered to said film layer bottom side.

18. The dressing of claim 17, wherein said absorbent pad is generally disposed in or adjacent to said insertion site viewing portion.

19. The dressing of claim 17, wherein said absorbent pad is generally disposed outside of said antimicrobial member.

20. The dressing of claim 17, including an absorbent pad link member that connects said absorbent pad to said antimicrobial member.

21. The dressing of claim 1, including a release liner releasably mounted directly on a portion of said transparent film layer bottom side.

22. A dressing comprising:
    a foldable fabric layer having an opening therein;
    a foldable transparent film layer having a top side, an opposite bottom side, and an outer periphery, wherein the opening of the fabric layer cooperates with the foldable transparent film layer to define an insertion site viewing portion; wherein the insertion site viewing portion is disposed within the outer periphery of the film layer, said bottom side having an adhesive portion and an adhesive-free portion, said adhesive-free portion being disposed within said insertion site viewing portion; and an antimicrobial member having a top side and an opposite bottom side, said antimicrobial member being disposed beneath the transparent film layer and within the outer periphery of the film layer in said insertion site viewing portion, a portion of said antimicrobial member being adhered to said film layer adhesive portion, and a portion of said antimicrobial member being disposed in said adhesive-free portion;

said antimicrobial member including an outer edge and a slit, wherein an end portion of said slit is disposed inboard of said outer edge, said slit being disposed adjacent said adhesive-free portion of the transparent film layer;

wherein the foldable film transparent layer completely covers the slit; and wherein said antimicrobial member is cooperable with a catheter extending from an insertion site on a patient such that said catheter extends through said slit in said antimicrobial member and said antimicrobial member surrounds said insertion site when said dressing is applied to said patient.

23. A dressing comprising:

a foldable transparent film layer having a top side, an opposite bottom side, and an insertion site viewing portion, said bottom side having an adhesive portion and an adhesive-free portion, said adhesive-free portion being disposed within said insertion site viewing portion; and an antimicrobial member having a top side and an opposite bottom side, said antimicrobial member being disposed beneath the transparent film layer in said insertion site viewing portion and inboard of an outer periphery of the transparent film layer, a portion of said antimicrobial member being adhered to said film layer adhesive portion;

said antimicrobial member defined by an outer edge and having a slot defined by an end portion, wherein the slot extends from a portion of the outer edge that is portioned inboard of the outer periphery of the transparent film layer, such that the end portion is positioned inboard of said outer edge and wherein an outermost portion of said outer edge of said antimicrobial member is disposed within said adhesive-free portion such that said outer edge is spaced from a boundary of said adhesive-free portion such that a gap between said outer edge and said boundary of said adhesive-free portion is at least 0.0625 to 0.125 of an inch in width;

wherein said antimicrobial member is cooperative with a catheter extending from an insertion site on a patient such that said catheter extends through said slot in said antimicrobial member and said antimicrobial member surrounds said insertion site when said dressing is applied to said patient.

24. A dressing comprising:

a foldable transparent film layer having a top side, an opposite bottom side, and an insertion site viewing portion, said bottom side having an adhesive portion and an adhesive-free portion, said adhesive-free portion being disposed within said insertion site viewing portion;

an antimicrobial member having a top side and an opposite bottom side, said antimicrobial member being disposed beneath the transparent film layer in said insertion site viewing portion and inboard of an outer periphery of the transparent film layer, a portion of said antimicrobial member being adhered to said film layer adhesive portion;

said antimicrobial member defined by an outer edge and having a slot defined by an end portion, wherein the slot extends from a portion of the outer edge that is portioned inboard of the outer periphery of the transparent film layer, such that the end portion is positioned inboard of said outer edge;

wherein said antimicrobial member cooperates with a catheter extending from an insertion site on a patient such that said catheter extends through said slot in said antimicrobial member and said antimicrobial member surrounds said insertion site when said dressing is applied to said patient; and a release liner releasably mounted directly on a portion of said transparent film layer bottom side, wherein said release liner includes a first member and a second member, each of the first member and second member including a mounted portion mounted on a portion of said transparent film layer and a gripping tab portion folded relative to said mounted portion;

said release liner further including a third member, said third member being mounted on a portion of said transparent film layer intermediate said first and second member, and said third member extending over said gripping tab portions of said first and second members, wherein said third member is releasable from said transparent film layer without tampering with said first and second members, and each of said first and second members is releasable from said transparent film layer without tampering with the other of said first and second members.

* * * * *